(12) United States Patent
Marcus et al.

(10) Patent No.: US 7,740,763 B2
(45) Date of Patent: Jun. 22, 2010

(54) CAPILLARY-CHANNELED POLYMERIC FIBER AS SOLID PHASE EXTRACTION MEDIA

(75) Inventors: R. Kenneth Marcus, Clemson, SC (US); Philip J. Brown, Williamston, SC (US); Igor A. Luzinov, Central, SC (US); Yonnie S. Wu, Seneca, SC (US)

(73) Assignee: Clemson University

( * ) Notice: Subject to any disclaimer, the term of this patent is extended or adjusted under 35 U.S.C. 154(b) by 977 days.

(21) Appl. No.: 11/373,900

(22) Filed: Mar. 13, 2006

(65) Prior Publication Data

US 2006/0201881 A1 Sep. 14, 2006

Related U.S. Application Data

(63) Continuation-in-part of application No. 10/915,735, filed on Aug. 10, 2004, now Pat. No. 7,261,813.

(51) Int. Cl.
*B01D 15/08* (2006.01)
(52) U.S. Cl. .............. 210/635; 210/638; 210/656; 210/198.2; 210/502.1; 210/510.1
(58) Field of Classification Search .............. 210/656, 210/635, 638, 500.23, 502.1, 510.1
See application file for complete search history.

(56) References Cited

U.S. PATENT DOCUMENTS

| 4,111,815 A | 9/1978 | Walker et al. |
| 4,187,333 A | 2/1980 | Rembaum et al. |
| 4,286,005 A | 8/1981 | Berger |
| 4,341,635 A * | 7/1982 | Golias .............. 210/656 |

(Continued)

FOREIGN PATENT DOCUMENTS

EP 0211206 A 2/1987

(Continued)

OTHER PUBLICATIONS

Article—*A capillary-scale liquid chromatography system that improves the practical sensitivity of HPLC-MS (MS) analysis*, Steven Cohen and Brian J. Murphy, Mar. 1999, pp. 28-32.

(Continued)

*Primary Examiner*—Ernest G Therkorn
(74) *Attorney, Agent, or Firm*—Dority & Manning, P.A.

(57) ABSTRACT

Solid phase extraction devices including a plurality of packed nominally aligned capillary-channeled polymeric fibers for use as stationary phase materials are disclosed. A plurality of fibers are packed together in a casing so as to provide good flow characteristics through the fibers and high surface area contact between a sample and the fibers. Different polymer compositions of the fibers permit the "chemical tuning" of the extraction process. The fibers can be physically or chemically derivatized to target specific analytes for separation from a test sample. Use of the fibers allows a wide range of liquid flow rates with very low backpressures. The fibers are easily packed into a micropipette tip or a conduit for use with a fluid flow device such as an aspirator or a pump. The devices can be used for isolation and pre-concentration of analytes from samples, for instance for proteins from buffer solutions or extraction of pollutants from remote locations.

17 Claims, 12 Drawing Sheets

U.S. PATENT DOCUMENTS

| | | | |
|---|---|---|---|
| 4,354,889 A | 10/1982 | Berger | |
| 4,391,716 A | 7/1983 | McCurry | |
| 4,657,742 A | 4/1987 | Beaver | |
| 4,729,808 A | 3/1988 | Berger | |
| 4,957,620 A | 9/1990 | Cussler | |
| 4,996,107 A | 2/1991 | Raynolds et al. | |
| 5,160,627 A | 11/1992 | Cussler | |
| 5,184,192 A | 2/1993 | Gilby et al. | |
| 5,225,079 A | 7/1993 | Saito et al. | |
| 5,234,594 A | 8/1993 | Tonucci et al. | |
| 5,277,821 A | 1/1994 | Coughlin et al. | |
| 5,395,521 A * | 3/1995 | Jagadeeswaran | 210/198.2 |
| 5,443,734 A * | 8/1995 | Fetner et al. | 210/656 |
| 5,604,012 A | 2/1997 | Okamoto et al. | |
| 5,800,897 A | 9/1998 | Sharma et al. | |
| 5,827,745 A | 10/1998 | Astle | |
| 5,855,798 A | 1/1999 | Phillips et al. | |
| 5,876,918 A * | 3/1999 | Wainwright et al. | 435/4 |
| 5,961,678 A | 10/1999 | Pruette et al. | |
| 5,972,505 A | 10/1999 | Phillips et al. | |
| 6,190,559 B1 * | 2/2001 | Valaskovic | 210/656 |
| 6,270,674 B1 | 8/2001 | Baurmeister et al. | |
| 6,616,723 B2 | 9/2003 | Berger | |
| 6,656,360 B2 | 12/2003 | Rohrbach et al. | |
| 6,780,314 B2 * | 8/2004 | Jinno et al. | 210/198.2 |
| 6,998,047 B1 * | 2/2006 | Kopaciewicz et al. | 210/321.75 |
| 7,083,723 B2 * | 8/2006 | Tubbs et al. | 210/198.2 |
| 7,166,212 B2 * | 1/2007 | Belov et al. | 210/198.2 |
| 2004/0020845 A1 | 2/2004 | Suzuki | |
| 2005/0023221 A1 | 2/2005 | Marcus | |
| 2005/0211615 A1 * | 9/2005 | DiLeo et al. | 210/198.2 |

FOREIGN PATENT DOCUMENTS

WO     WO03/022393 A1     3/2003

OTHER PUBLICATIONS

Article—*A Novel Stationary Phase: Capillary-Channeled Polymer (C-CP) Fibers for HPLC Separations of Proteins*, Dwella K. Nelson and R. Kenneth Marcus, Journal of Chromatographic Science, vol. 41, Oct. 2003, pp. 475-479.

Article—*Capillary-channeled polymer fibers as stationary phases in liquid chromatography separations*, R. Kenneth Marcus, W. Clay Davis, Brad C. Knippel, LaTasha LaMotte, Teresa A. Hill, Dvora Perahia, and J. David Jenkins, Journal of Chromatography A, vol. 986, 2003, pp. 17-31.

Article—*Micropipette Tip—Based Sample Preparation for Bioanalysis*, Majors et al., LCGC North America—Solutions for Separation Scientists, Jul. 1, 2005, 6 pages, www.lcgcmag.com.

Marcus, et al., "Fiber Bundle Cartiridges as Chemical Separation Media", US Patent No. 7,261,813, issued Aug. 28, 2007.

* cited by examiner

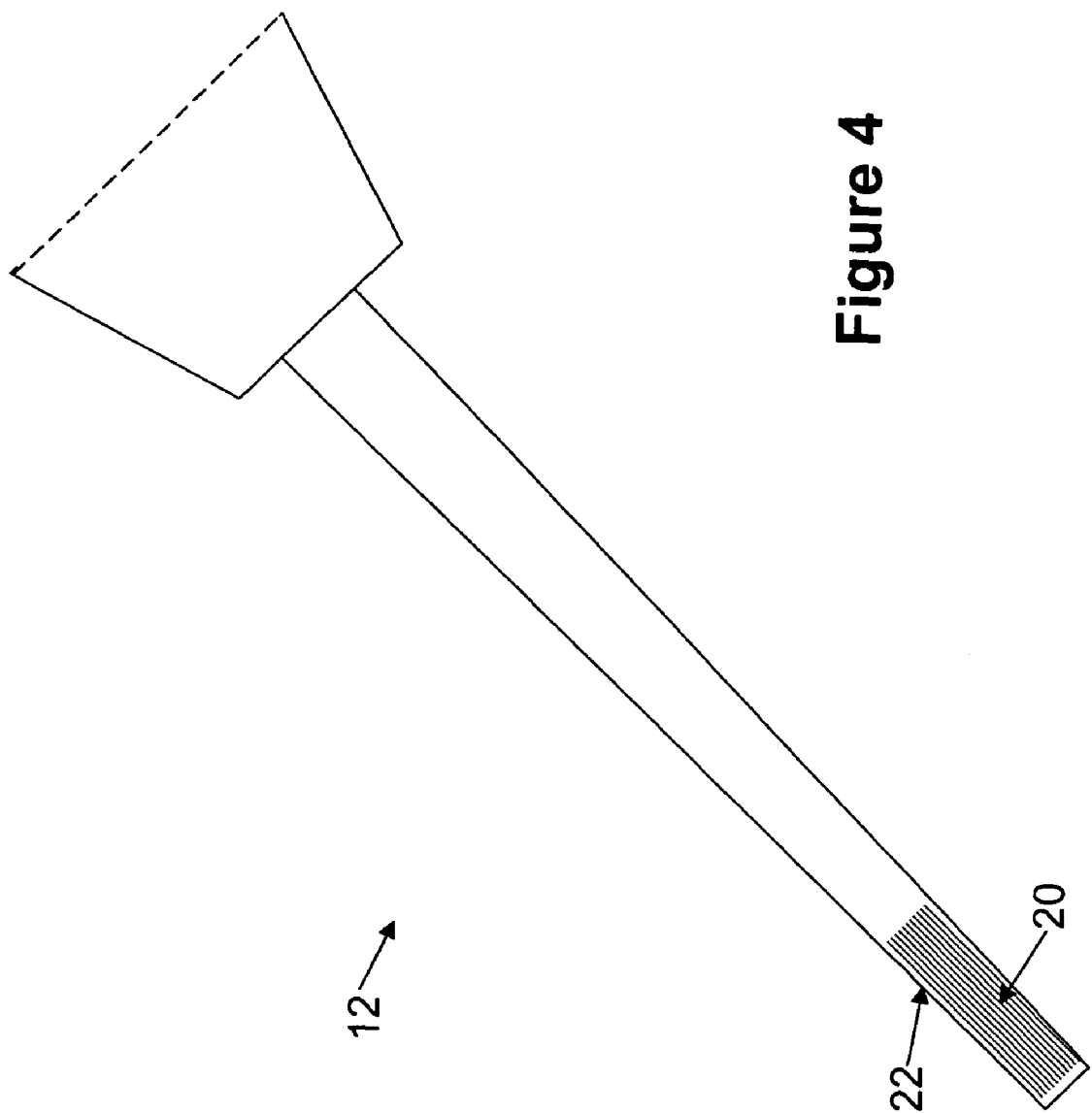

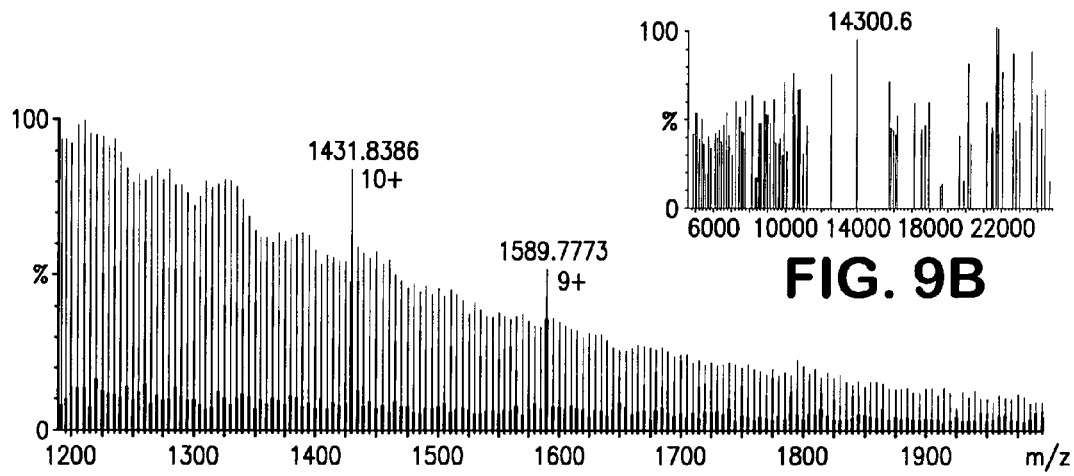
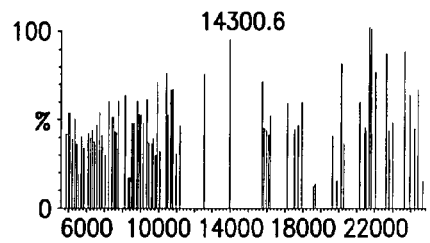
FIG. 9A
FIG. 9B
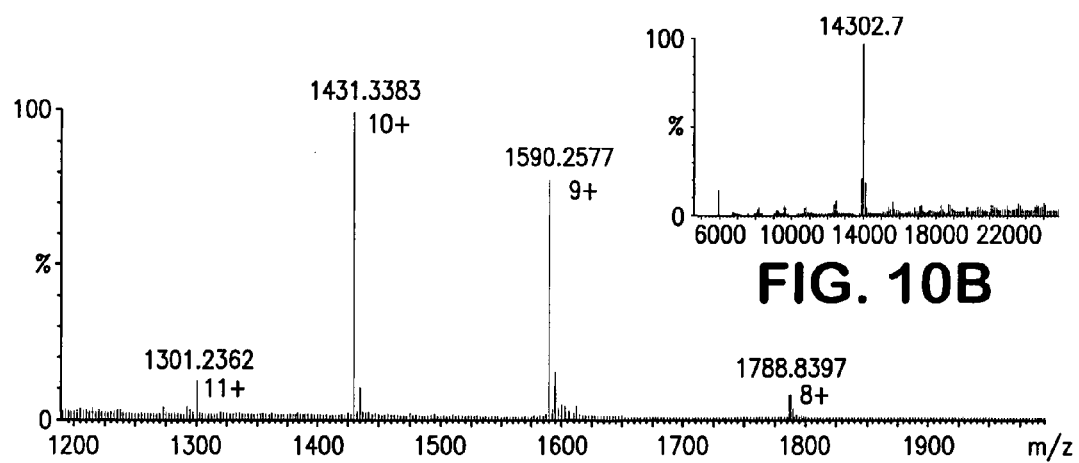
FIG. 10A
FIG. 10B

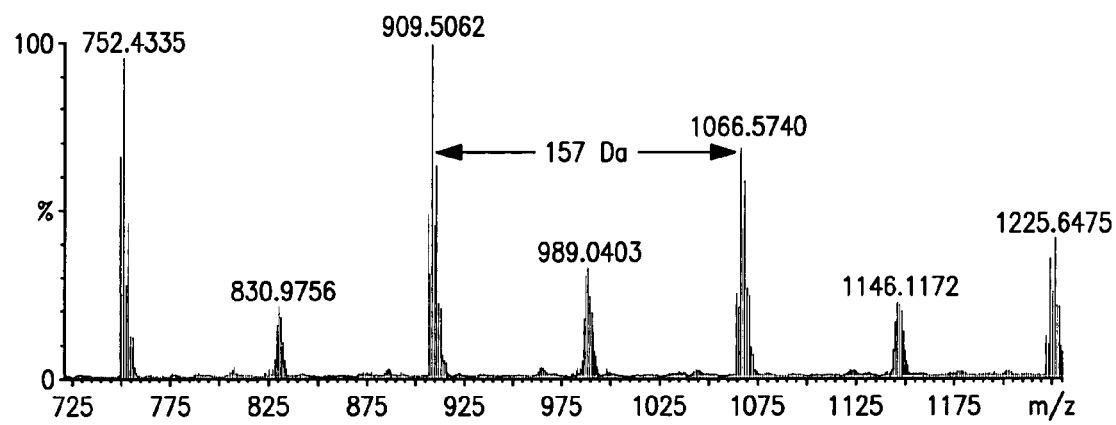
FIG. 11
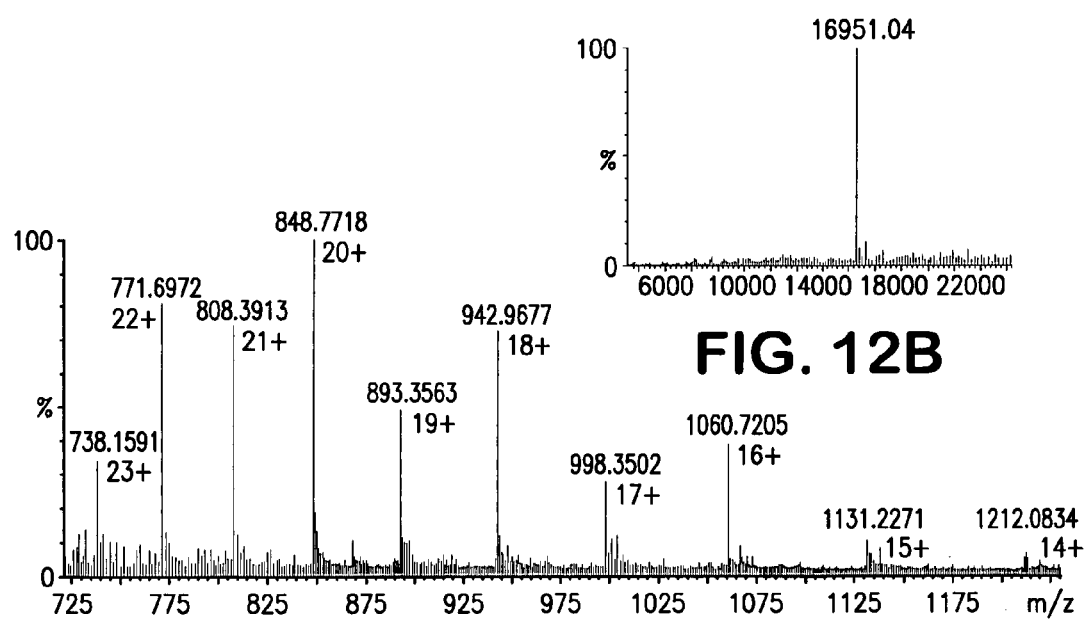
FIG. 12B
FIG. 12A

US 7,740,763 B2

CAPILLARY-CHANNELED POLYMERIC FIBER AS SOLID PHASE EXTRACTION MEDIA

CROSS REFERENCE TO RELATED APPLICATION

This application is a continuation-in-part application of U.S. patent application Ser. No. 10/915,735 filed on Aug. 10, 2004, now issued U.S. Pat. No. 7,261,813.

BACKGROUND OF THE INVENTION

The ability to extract a targeted analyte from a fluid sample has proven to be of great assistance in a variety of analytical applications. For instance, the ability to assay the contents of test samples has proven extremely useful in the testing and examination of biological samples, in particular as analytical testing of biological samples often calls for a wide variety of tests and examinations from a starting sample of a very small volume. In general, micropipettes are used for the handling of these small sample volumes.

The formation of micropipette tips to include a variety of chemistries by packing, coating, or embedding a suitable phase in the tip or on the tip walls has led to the development of micropipette solid phase extraction (SPE) techniques including affinity interactions, hydrophobic interaction, hydrophilic interaction, ion exchange, reverse phase, and the like. This, in turn, has led to improved processing of the samples. For instance, proteins and peptides are often found in buffered solutions that can also contain components such as inorganic salts, low molecular weight organics, urea and detergents. Micropipette SPE tips have been successfully used to isolate the targeted polypeptides from such components prior to characterization and thereby improve the detection limits and the sensitivity of the characterizations.

Problems exist with known devices, however. For instance, many phases that are proposed for use with micropipette tips are limited in possible chemistries. In addition, the sorbent media are often very expensive to prepare and can be quite fragile and easily damaged. Moreover, in designing the devices, e.g., the micropipette SPE tips, there is often a necessary trade-off between surface area available for reaction and efficient fluid transport through the device, i.e., in order to increase available reactive surface area, fluid transport is detrimentally effected, and vice versa. Existing SPE media are often packed into micropipette tips via a porous bead or a monolithic stationary phase. Flow through such media is inefficient, however, and a series of successive aspiration steps is usually required to improve removal efficiency of the process. These additional steps add to the time of sample preparation as well as the complexity of the equipment required.

What is needed in the art are improved sorbent media for SPE applications that can address these and other problems in the art.

SUMMARY OF THE INVENTION

In one embodiment, the present invention is directed to a device that can be utilized in solid phase extraction. For instance, the device can include a plurality of nominally aligned polymeric fibers disposed within a casing. An analyte in a test sample can exhibit an affinity for the fibers and thus the fibers can function as the sorbent media in an SPE process. The fibers can define a plurality of co-linear capillaries (optionally referred to throughout this application as channels) along their length. In one embodiment, the test sample can contact the surface of the sorbent media via capillary action of the sample through the capillaries of the fibers. As the sample contacts the fibers, the analyte can preferentially adsorb to the surface of the fibers due to an affinity of the analyte for the fiber that can be, for instance, an ionic, chemical, hydrophobic, or hydrophilic affinity. Following extraction, the analyte can be eluted back off of the sorbent media, for instance for further examination or characterization.

In one embodiment, the casing surrounding the fibers can be a portion of a micropipette tip. In another embodiment, the casing can be a portion of a stand-alone separation device that can be removably attached to a fluid flow device. For instance, the packed casing can be removably attachable to an aspirator, a pump, an electro-osmosis device, or any other suitable hydro-dynamic device. The SPE device including the casing packed with the fibers can provide a large surface area for contact between a test sample and the fibers while simultaneously providing good flow characteristics for a fluid through the packed casing. Accordingly, the devices can be beneficially utilized for extraction of an analyte from a test sample, for instance for isolation or concentration protocols. In one embodiment, the packed casing can form a portable SPE device that can be utilized for extraction of analytes from remote locations.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which:

FIG. 1A is an expanded view window showing a cross-section of the packed conduit of FIG. 1.

FIG. 4 is a schematic representation of a micropipette tip, the end of which is packed with a plurality of capillary-channeled polymeric fibers as herein described.

FIG. 9A illustrates the electrospray ionization mass spectrum (ESI-MS) of lysozyme from chicken egg white in a phosphate-buffered saline (PBS) matrix.

FIG. 9B illustrates the deconvoluted ESI-MS spectrum of FIG. 9A.

FIG. 10A illustrates the ESI-MS of lysozyme from chicken egg white following extraction of the lysozyme from the PBS matrix onto the polypropylene capillary-channeled fibers packed into a casing as herein describe, the packed casing having been mounted in conjunction with a micropipette tip.

FIG. 10B illustrates the deconvoluted ESI-MS spectrum of FIG. 10A.

FIG. 11 illustrates the ESI-MS of myoglobin from equine skeletal muscle in a tris buffer matrix.

FIG. 12A illustrates the ESI-MS of myoglobin from equine skeletal muscle following extraction of the myoglobin from the tris buffer matrix onto polypropylene capillary-channeled fibers packed into a casing as herein describe, the packed casing having been mounted in conjunction with a micropipette tip.

FIG. 12B illustrates the deconvoluted ESI-MS spectrum of FIG. 12A.

The same reference characters designate the same or like components throughout the drawings and description.

DETAILED DESCRIPTION OF REPRESENTATIVE EMBODIMENTS

Definitions

Figure 1:
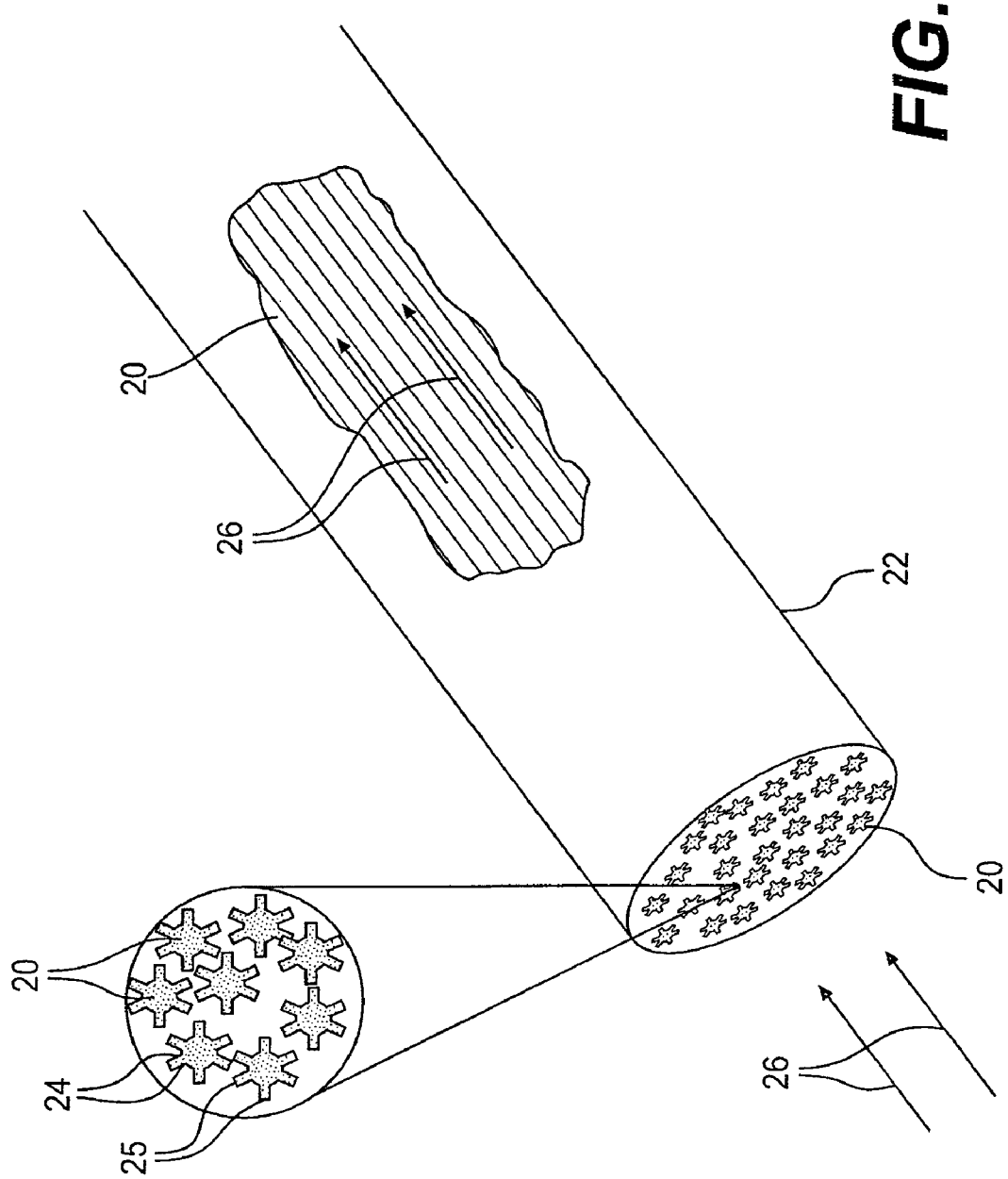
FIG. 1 is a schematic representation of one embodiment of a conduit packed with a plurality of capillary-channeled polymeric fibers that can be utilized for an SPE as herein described.

As used herein, the term "test sample" generally refers to any material suspected of containing an analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production examinations. The test sample may be used directly as obtained from the source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

As used herein, the term "protein" refers to any molecular chain of amino acids that is capable of interacting structurally, enzymatically or otherwise with other proteins, polypeptides or any other organic or inorganic molecule.

As used herein, the term "polypeptide" refers to a molecular chain of amino acids and does not refer to a specific length of the product. Thus, peptides, oligopeptides and proteins are included within the definition of polypeptide. This term is also intended to include polypeptides that have been subjected to post-expression modifications such as, for example, glycosylations, acetylations, phosphorylations, and so forth.

DETAILED DESCRIPTION

Reference will now be made in detail to various embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

In general, the present invention is directed to methods and devices that can be utilized in performing phase extraction (SPE) protocols. In one embodiment, the present invention is directed to small volume SPE protocols, for instance for fluid samples of less than about 1 milliliter (mL) in volume. In other embodiments, however, the methods and devices disclosed herein can be utilized for extraction of an analyte from larger samples, for instance, up to about 5 mL in volume, or larger samples in other embodiments, up to about 10 mL in volume, or larger yet in other embodiments. Representative devices can, for example, include a casing packed with the disclosed sorbent media to form an extraction conduit that can be removably attached to a fluid flow system, for instance a system including an aspirator, a pump, or the like. In another embodiment, a device or system for moving fluid through the conduit is not necessary, and the fluid can merely be wicked through the conduit via the capillary action of the fibers. In yet another embodiment, the present invention is directed to a micropipette tip packed with the sorbent media as herein described.

According to the present invention, capillary-channeled polymeric fibers can be beneficially utilized as sorbent media for SPE protocols. In one preferred embodiment, the capillary-channeled polymeric fibers utilized can be similar to those disclosed in U.S. Patent Application Publication 2005/0023221 to Marcus, which is incorporated herein in its entirety by reference.

Figure 2:
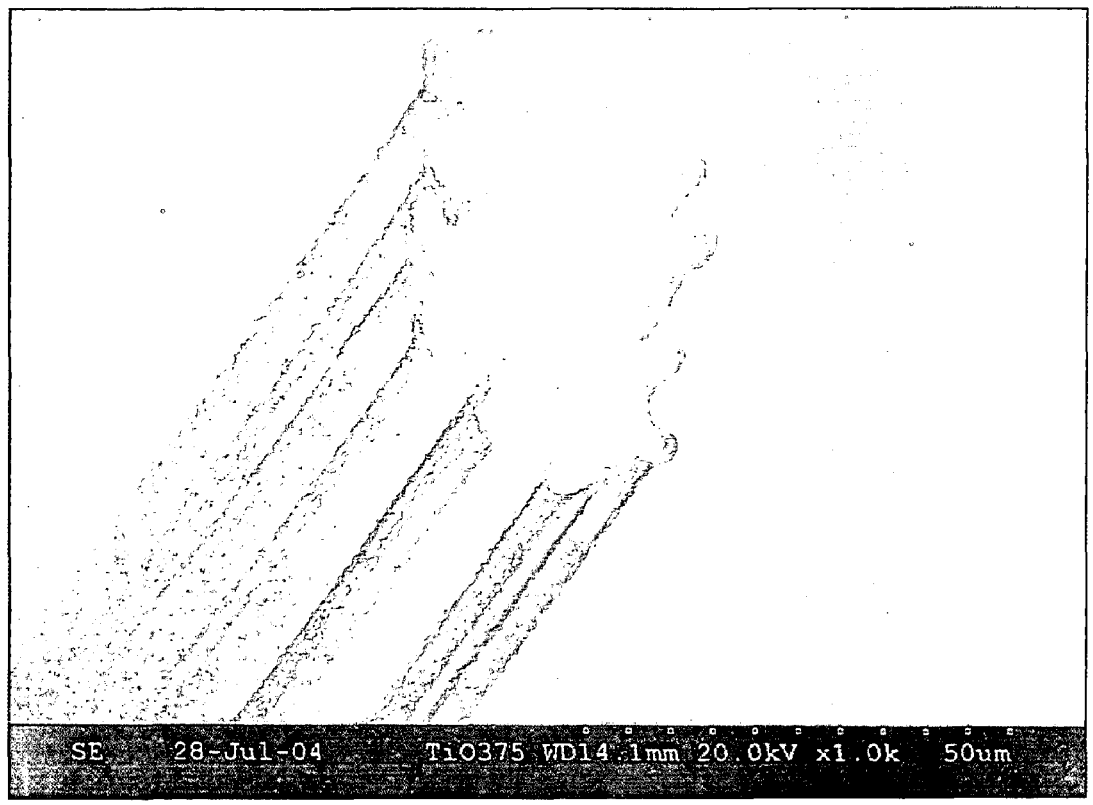
FIG. 2 is a micrograph of two interdigitated capillary-channeled polymeric fibers as herein described.

Referring to FIG. 1, a plurality of capillary-channeled polymeric fibers 20 are shown packed into a casing 22. FIG. 1 also includes an inset at 1A that illustrates one possible embodiment of the capillary-channeled fibers. As shown schematically in cross-section in the expanded view window of FIG. 1A, each fiber strand 20 has six co-linear capillaries 24 extending the entire length of the exterior surface of the fiber 20. Each capillary 24 is defined by a pair of opposed walls 25 that extend generally and longitudinally and form part of the exterior surface of the fiber 20. Desirably, these capillaries 24 and walls 25 extend down the entire length of the fiber 20 parallel to the longitudinal axis of the fiber 20 and are nominally co-linear on each fiber 20. This produces de facto substantially the same co-linear capillaries 24 along the entire length of the casing 22. FIG. 2 is a micrograph of two exemplary capillary-channeled polyester fibers as may be utilized as herein described. FIG. 2 illustrates the interdigitation of the fibers as may occur during packing of the fibers that may improve the capillary flow of a fluid through a packed conduit. It should be understood that the particular shapes of the capillary-channeled fibers illustrated in FIGS. 1 and 2 are not a requirement of the present invention. In particular, the number and/or cross-sectional shape of the capillaries as well as the overall shape of the capillary-channeled fibers can vary from that shown in the figures.

In one embodiment, the capillaries 24 can be configured to wrap around the length of the fiber 20 in a helical fashion. In one embodiment, substantially all of the capillaries 24 can be nominally co-linear on each fiber 20. As such, substantially all of the capillaries 24 of a plurality of fibers 20 can follow a helix pattern that has a similar pitch. The pitch is the number of complete turns of a single capillary 24 around the circumference of the fiber 20 per unit of length of the fiber 20. This also can produce de facto substantially the same co-linear capillaries 24 along the entire length of the casing 22.

Additionally, in the course of packing the fibers 20 into a bundle that lays along the entire length of the casing 22, whether the individual fibers have purely linear capillaries 24 or helical ones, it is possible that one or more, even all, of the fibers 20 in the bundle will rotate about its/their own axis or the axis of the casing 22 over the entire length of the column. In other words, the capillary-channeled fibers 20 may twist as they lay within the casing 22. Accordingly, the capillaries 24 and walls 25 also may twist somewhat.

In some embodiments of the present invention, a device can be provided to move fluid through the casing 22 and thus through the capillaries 24 of the fibers 20. For instance, a fluid sample can be aspirated through the casing 22 by any suitable aspiration system as is known in the art. The flow of liquid through the casing 22 is schematically indicated by the arrows designated by the numeral 26 in FIG. 1. A portion of the casing 22 is cut away in the view shown in FIG. 1 for the purpose of illustrating the flow of liquid 26 through the casing 22 along the fibers 20 arranged with their longitudinal axes parallel to the longitudinal axis of the casing 22.

Use of an aspirator is not a requirement, however, and in those embodiments in which a device is used to move fluid through the conduit, any method as is generally known in the art for moving a fluid through the casing 22 may be utilized. For example, in other embodiments, electro-osmosis, pumps, injectors, or any other suitable hydro-dynamic means may be utilized to move fluid through the casing 22.

In other applications, the movement of the fluid may be effected without a device that is separate from the fibers themselves. In such embodiments, the fluid can, for instance, move through the capillaries 24 of the fibers 20 solely by capillary action. In general use, the capillary-channeled polymer fibers 20 can have a very strong wicking action for a variety of liquids, including water.

Advantageous in the use of these capillary-channeled polymer fibers 20 as stationary phase materials is their high surface area-to-volume ratios. Moreover, the shape and the number of capillaries 24 can be dependent on achieving the desired attribute of very high surface area-to-volume ratios. In this regard, helical capillaries 24 can pack more surface area than linear capillaries 24 and thus may be preferred, in some embodiments.

Another advantage of using capillary-channeled polymer fibers 20 in the disclosed processes is the fact that they generate very low backpressures (e.g., 500 to 1500 psi for linear capillaries 24 for normal chromatography flow rates (0.5 to 3 mL/min). The lower backpressure produced in the casing 22 containing capillary-channeled polymer fibers 20 relative to the backpressure produced as compared to that produced by, for instance packed beads or monolithic sorbent media, and is believed to be due at least in part to the parallel-running capillaries 24. The ability to use fibers 20 of any desired length, while encountering relatively low backpressures, would suggest great potential for using conduits packed with these capillary-channeled polymer fibers 20 in a variety of applications including SPE as described herein.

Yet another advantage of utilizing the capillary-channeled polymer fibers in the disclosed SPE protocols is the ease of packing such materials into a casing. For instance, existing SPE media are often in the form of micro-beads or a monolithic stationary phase, both of which can be very difficult to pack and contain as desired within the flow field. For instance, in order to contain a plurality of micro-beads or a monolithic stationary phase, micropipette SPE tips often require some sort of perforated containment barrier, internal wall projections, or the like to hold the sorbent media within the tip. No such devices are required for the sorbent media disclosed herein, as the capillary-channeled polymeric fibers 20 can be merely pulled through and packed within a casing 22, for instance via use of a monofilament line as is further described herein, with no additional containment device necessary to hold the fibers in place. It can be a fairly simple process to pack the fibers tightly enough so as to ensure they will be securely maintained in the casing during an SPE protocol. Moreover, even with tight packing, excellent flow characteristics of a fluid through the packed conduit can be attained. For instance, a plurality of fibers 20 can be packed into casing 22 tightly enough to prevent movement of the media under typical SPE pressures while maintaining a interstitial fraction within the casing of between about 0.15 and about 0.7, for instance about 0.6, so as to provide excellent flow characteristics through the packed casing while still providing good contact between the solid phase sorbent media and the fluid sample passing through the casing.

There are many different fabrication approaches that can be utilized to form capillary-channeled polymeric fibers 20 of the sort demonstrated here. For instance, the capillary-channeled polymeric fibers 20 are amenable to formation from any polymers that can be melt spun. A non-limiting list of exemplary materials from which the fibers can be formed can include polyolefin precursors, such as polypropylene, polyethylene, polybutylene, and the like, polyester precursors, polyaniline precursors, precursors composed of polylactic acid, and polyamide precursors such as nylon precursors. Moreover, the formed polymeric fibers can include a mix of polymers and/or copolymers, including random copolymers and block copolymers of any monomeric or oligomeric precursor.

The fibers can be formed to a desired size and shape, for instance to promote capillary flow of a liquid with a predetermined viscosity through the casing. For instance, the nominal diameter of each fiber 20 (i.e., the diameter of the fiber encompassing the surface capillaries) can range between about 10 and about 80 micrometers (µm). The depth of a single capillary on a fiber, i.e., the radial height of walls 25 on FIG. 1A, can range, for instance, between about 1 µm and about 20 µm.

In general, casing 22 can be of any material compatible with an SPE protocol. For example, casing 22 can be a glass, ceramic, metallic or polymeric material. In one embodiment, casing 22 can be formed of the same or similar polymeric material as is used to form fibers 20. For instance, casing 22 can be formed of the same base polymer as is used to form the capillary-channeled fibers 22, though the finished materials may vary somewhat with regard to additives such as clarifiers, nucleating agents, stabilizing agents, other polymers or polymer components, and the like. According to this embodiment, the available surface area for interaction between the sorbent media and the sample can be even greater, as it can also include the interior contact surface of casing 22.

Figure 3:
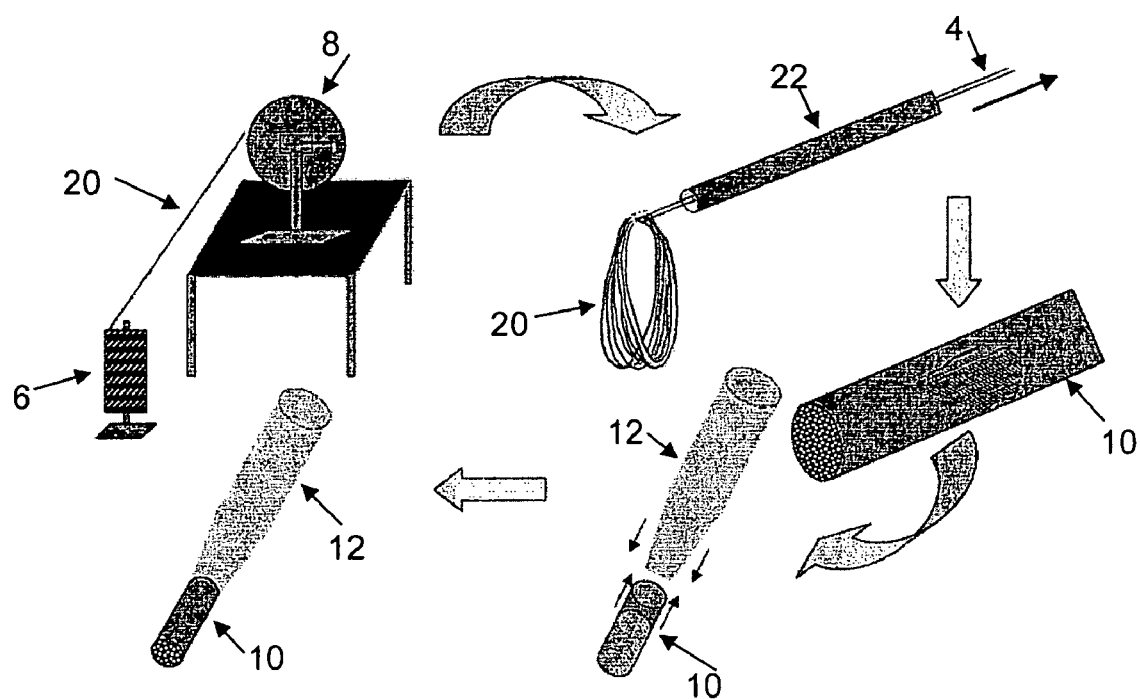
FIG. 3 is a schematic representation of one embodiment for forming a portable extraction conduit as herein described.

According to one embodiment, casing 22 can form the body of a detachable extraction conduit 10 as is illustrated in FIG. 3. A detachable extraction conduit 10 can be used in large or small volume SPE protocols, as desired. For instance, extraction conduit 10 can be removably attachable to a micropipette tip for use in a small volume micropipette SPE protocol. Accordingly, an extraction conduit 10 can be of a cross-sectional shape and size so as to be removably attachable to a micropipette tip. The present invention is not limited to small volume SPE protocols, however, and the extraction conduits disclosed herein can be utilized in larger volume protocols as well. According to this embodiment, a single fluid flow device, e.g., an aspirator, can be utilized with a succession of removable extraction conduits, which can lead to lower costs and simplification of the SPE protocols.

In one embodiment, a detachable extraction conduit 10 can have an inner diameter between about 0.5 mm and about 5 mm. In another embodiment, the extraction conduit 10 can have an inner diameter between about 0.5 mm and about 1 mm, or larger yet in other embodiments. Of course, the extraction conduit need not be circular in cross section, and the present invention encompasses detachable extraction conduits and micropipette tips of any cross sectional geometry.

The preferred length of a detachable extraction conduit 10 can generally vary depending upon the particularities of the separation to be affected including volume of the test sample, flow velocity, analyte affinity for the fibers, etc. For example, when considering small volume separation protocols, i.e., less than about 1 mL in volume, an extraction conduit 10, can generally be between about 0.5 cm and about 3 cm in length. In other embodiments, however, extraction conduits as herein described can be longer, for instance up to about 10 cm in length, or even longer in other embodiments, for example when considering an SPE extraction for a large volume sample.

In one embodiment, the length of each fiber 20 can be substantially the same as the length of the casing 22. For instance the fibers 20 can be disposed to extend within the casing 22 over substantially the entire length of a detachable extraction conduit 10. However, fibers 20 that have lengths that are shorter than the length of the casing 22 may be used. Moreover, an SPE device can include fibers of various lengths.

FIG. 3 illustrates one method for forming and using a detachable extraction conduit 10. According to this particular embodiment, a capillary-channeled fiber 20 can be fed from a fiber spool 6 to a rotary counter 8. A loop of capillary-channeled polymer fiber 20 containing the desired number of wraps can then be removed from the rotary counter 8 and attached to a monofilament 4. The monofilament 4 can be used to pull the loop of capillary-channeled polymer fibers 20 through the casing 22. The casing 22 containing the fibers 20 can then be trimmed as desired to form the detachable extraction conduit 10. Prior to utilization in an SPE protocol, extraction conduit 10 can be removably attached to a fluid flow device, for instance a micropipette tip 12 as shown.

Utilization of a removably attachable extraction conduit 10 may be particularly beneficial when examining samples at remote locations. For instance, due to the excellent fluid flow and high wicking capabilities of the disclosed capillary-channeled fibers, SPE protocols can be carried out without the need for transporting hydro-dynamic devices. Moreover, in those embodiments in which a fluid flow device is used, a large number of extractions could be carried out with a minimal amount of equipment, as a single fluid flow device (e.g., pump, aspirator, etc.) could be utilized with several different extraction conduits in several consecutive separations, each designed for extraction of the same or a different analyte from the remote sample. Following return to a testing facility, the analytes could be eluted off of the extraction conduits for characterization in the laboratory setting.

Referring to FIG. 4, another embodiment of the present invention is illustrated in which the fibers 20 can be packed directly into the end of a micropipette tip 12 such that casing 22 is formed by the walls of the micropipette tip. As with the embodiment discussed above, the length of the fibers packed into the micropipette tip 12 can vary, depending upon the geometry of the micropipette tip 12 as well as the particular characteristics of the separation. In general, however, fibers 20 packed directly into a micropipette tip 12 can generally be between about 1 mm and about 30 mm in length.

The ability to perform chemical separation of otherwise similar compounds for mixtures of polyaromatic hydrocarbons (PAHs), lipids, organic and inorganic lead compounds, and proteins has been demonstrated. This capability is particularly surprising given the seemingly chemically benign polymer compositions that can be used to form the capillary-channeled polymeric fibers.

Figure 5A:
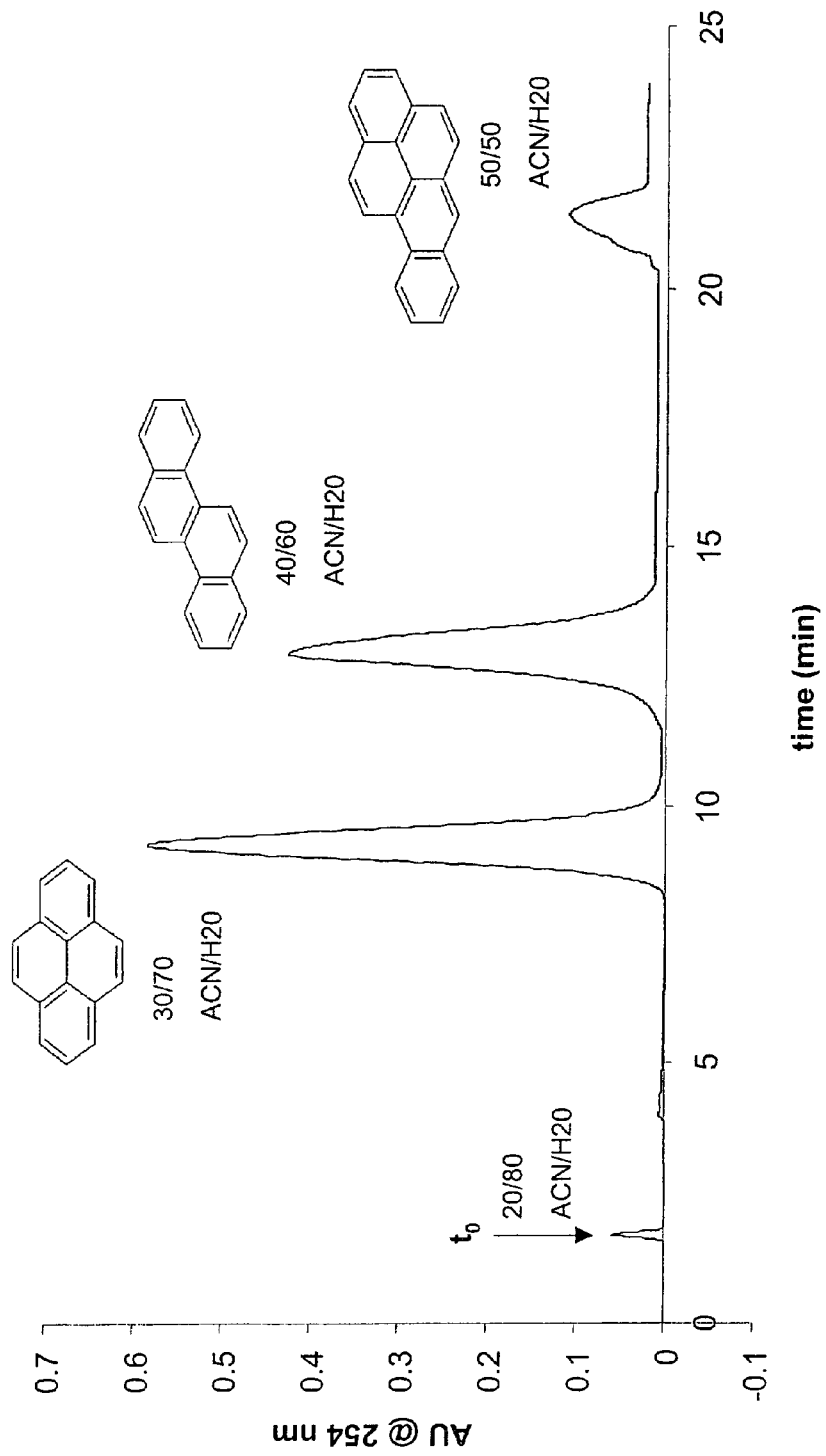
FIG. 5A is a graphical presentation of the time variation of absorbance that is illustrative of the separation of three polyaromatic hydrocarbons (PAH) compounds by capillary-channeled propylene fibers as may be used in the disclosed SPE protocols.
Figure 5B:
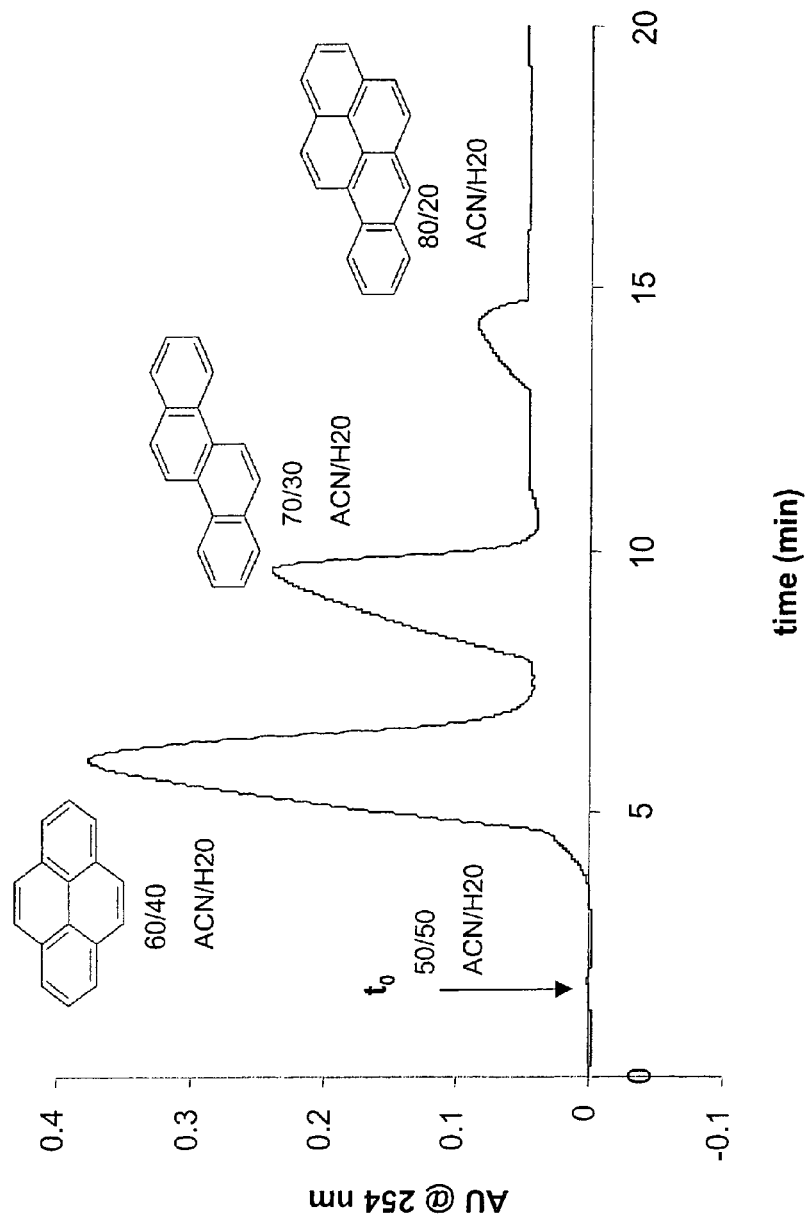
FIG. 5B is a graphical presentation of the time variation of absorbance that is illustrative of the separation of the same three PAH compounds shown in FIG. 5A by polyester capillary-channeled fibers as may be used in the disclosed SPE protocols.

FIG. 5A illustrates the separation of three different PAHs on a column filled with capillary-channeled polypropylene fibers. Similarly, FIG. 5B illustrates the separation of three PAHs on a column filled with capillary-channeled polyester fibers. As noted in FIGS. 5A and 5B, different relative concentrations of acetonitrile (ACN) to water were required to elute the solute species from the stationary phase and to obtain the chromatograms. Thus, gradient elution methods (i.e., changes in solvent composition) may be employed to elute the solute species from the stationary phase and to obtain the chromatograms. This is direct evidence of chemical interactions between the analyte molecules and the polymer fibers; as opposed to a more physical and mechanical "filtering" mechanism of retention of the species on the surfaces of the fibers.

Different from the use of channeled polymer fibers for the filtration of particulate matter in liquid and vapor streams, the use of capillary-channeled fibers as proposed here is clearly based on chemical interactions between the analyte/solutes and the surfaces of the polymer fibers. The fact that solvent gradients are required to separate the compounds as depicted in FIGS. 5A and 5B clearly demonstrates that this is the case. For example, the mixture of PAH's is completely immobilized on the polypropylene surface in aqueous solution to the point where the acetonitrile (ACN) concentration makes up 30% of the solvent composition. The same separation using polyester fibers as the stationary phase requires a 60% ACN to 40% $H_2O$ mixture; proving that the two polymers behave differently.

Liquid chromatography itself is based on the relative distribution between the solid and solution phases, and so relative retention characteristics are an excellent indicator of the actual interactions. The use of different combinations of polymer stationary phases, analyte/solutes, and mobile phases provides empirical insights into the retention processes.

Figure 6A:
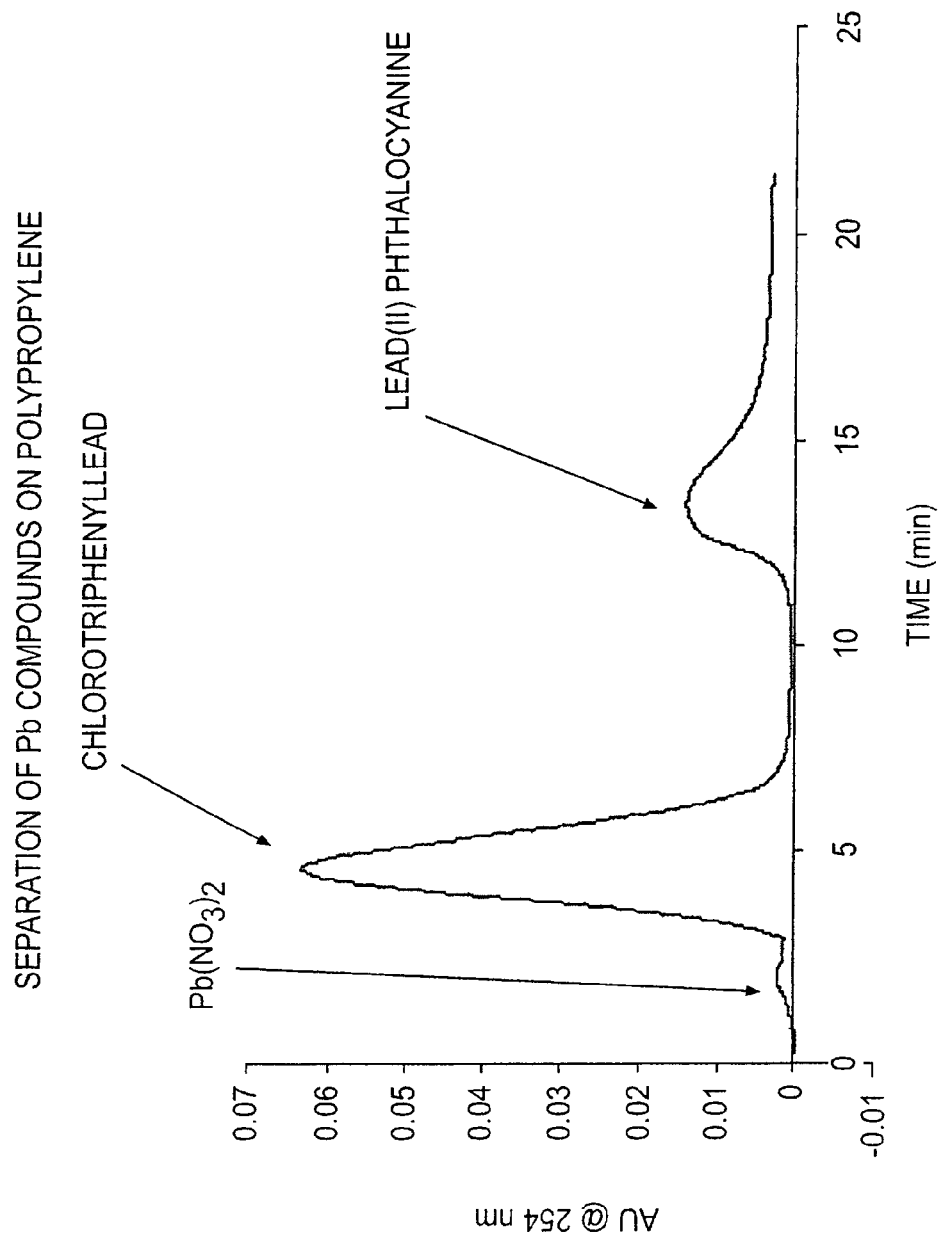
FIG. 6A is a graphical presentation of the time variation of absorbance that is illustrative of the separation of three lead-based compounds by propylene capillary-channeled fibers as may be used in the disclosed SPE protocols.
Figure 6B:
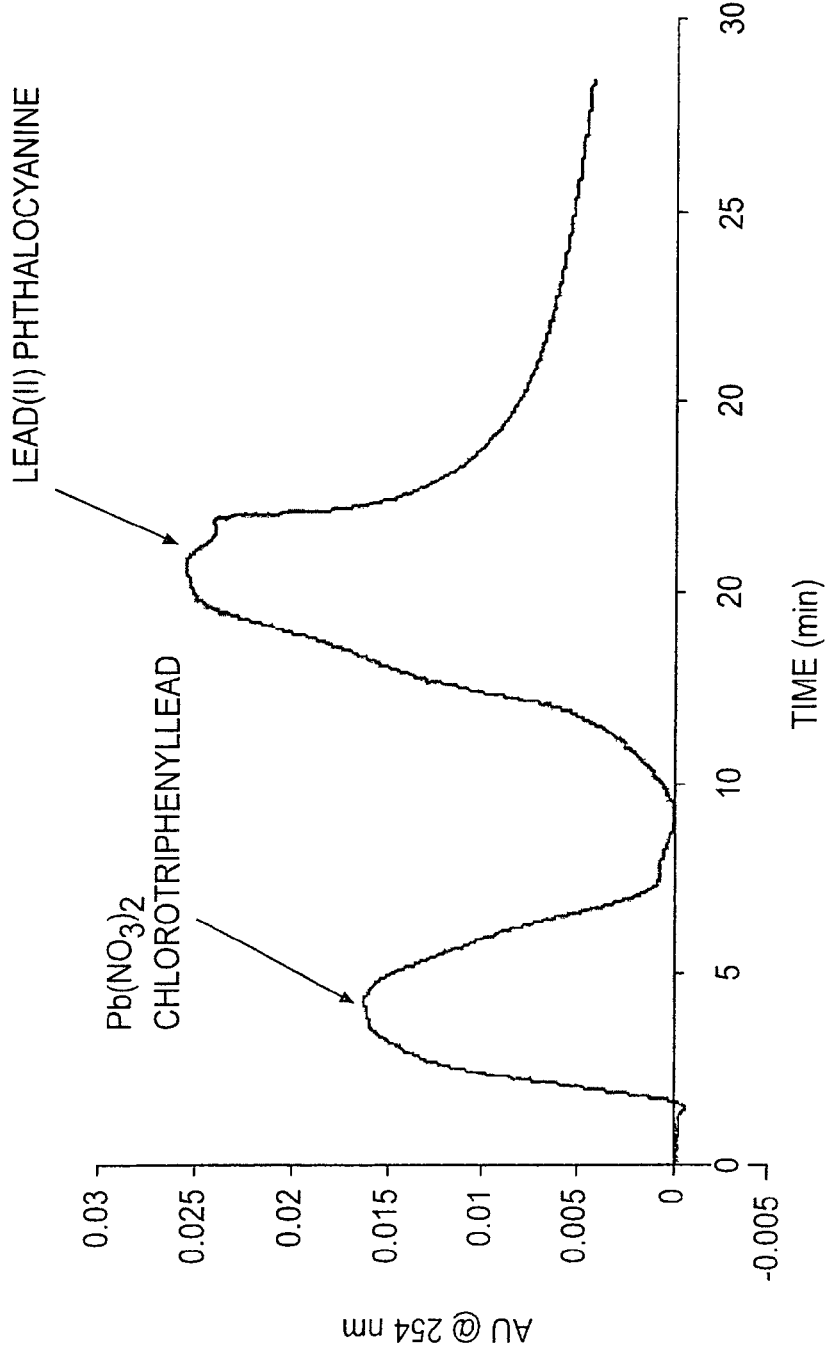
FIG. 6B is a graphical presentation of the time variation of absorbance that is illustrative of the separation of the same three lead-based compounds shown in FIG. 6A by polyester capillary-channeled fibers as may be used in the disclosed SPE protocols.

FIG. 6A illustrates the use of a column packed with capillary-channeled polypropylene fibers to separate three species of lead-based compounds. Similarly, FIG. 6B illustrates the separation of the species of these same three lead-based compounds using a column packed with capillary-channeled polyester fiber. The vertical axis in each of FIGS. 6A and 6B is a measure of the absorbance of light at 254 nanometers by each species. The greater the absorbance of that light, the higher the number of absorbance units (AU) that is recorded on the chromatogram. The horizontal axis is the time axis that measures how long it takes for the majority of the species (the peak) to be detected by the absorbance of the light at 254 nm. Referring to FIG. 6A for example, the chlorotriphenyllead species shows a peak reading of about 0.06 AU at 254 nm at 5 minutes after the 0.02 mL volume of solution containing the chlorotriphenyllead species was introduced into the column that was packed with the capillary-channeled polypropylene fiber.

FIG. 6A illustrates that the lead nitrate species has less of a strong interaction with the polypropylene fibers in the column than either the chlorotriphenyllead species or the lead (II) phthalocyanine. The lead nitrate peak (though barely above zero) occurs earlier in time than either of the peaks of the chlorotriphenyllead species or the lead (II) phthalocyanine species. Of the three lead-based species tested, the lead nitrate species has the least affinity for the polypropylene fibers in the column. Moreover, the lead nitrate species has a different affinity for the polypropylene fibers in the column because the lead nitrate species has a different chemistry than each of the chlorotriphenyllead species and the lead (II) phthalocyanine species.

Figure 7:
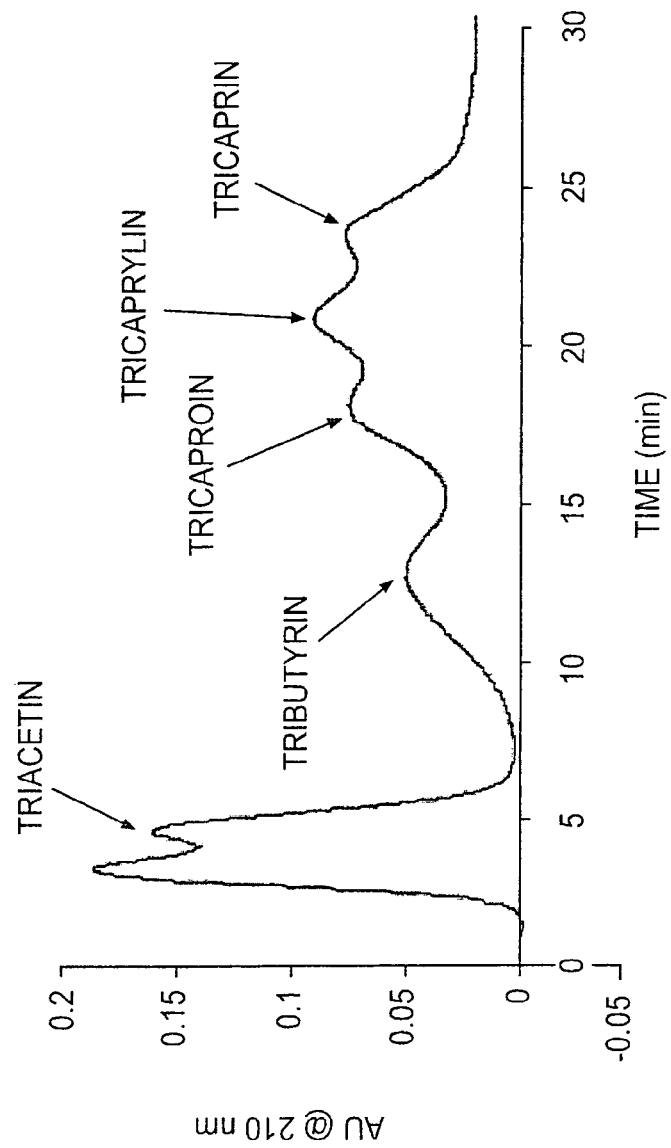
FIG. 7 is a graphical presentation of the time variation of absorbance that is illustrative of the separation of five lipid compounds by polyester capillary-channeled fibers as may be used in the disclosed SPE protocols.

FIG. 7 illustrates a similar separation protocol for a mixture including five different lipid compounds on a column packed with a plurality of capillary-channeled polyester fibers.

It should be understood that as FIGS. 5A, 5B, 6A, 6B, and 7 are based on absorbance of light at a particular wavelength, the peak height of each species doesn't necessarily reflect the relative concentrations of each of the species because each of them absorbs that wavelength with different strengths.

Beneficially, polymeric materials that can be utilized in forming the capillary-channeled fibers can be specifically tailored for extraction of a wide variety of classes of chemical compounds. Applications in analytical separations for a wide range of compound classes are anticipated by changing the identity of the base fiber or performing chemical derivatization of the surfaces of the fibers. For instance, in one embodiment, the polymeric materials used to form the fibers could be designed for a particular separation protocol. For example, polymeric fibers could be formed to include a particular ionic character, a particular hydrophobic/hydrophilic character, or even a particular reactivity so as to preferentially adsorb a specific analyte class from a fluid sample.

In one embodiment, the surfaces of the polymeric fibers could be modified following formation of the fibers while maintaining the high surface area-to-volume ratio and the basic structure. For instance, at least portions of the surfaces of the polymeric fibers can be modified to a predetermined chemical reactivity. For example, the predetermined chemical reactivity could be obtained by modifying at least portions of the surfaces of the polymeric fibers to a predetermined level of hydrophobicity. Thus, active sites on the fiber surfaces could be functionalized to gain more or less hydrophobic character. The predetermined chemical reactivity also could be obtained by modifying at least portions of the surfaces of the polymeric fibers to a predetermined ionic character. For example, the surfaces of fibers formed from polyvinyl alcohol (PVA) could be protonated in situ via an acidic mobile phase to produce an ion exchange column. Optionally, the fibers can be functionalized with an affinity ligand particular for the analyte of interest. For instance, the fibers can be surface treated with specific dyes, lectins, antibodies, and the like to show particular binding affinity for a biological analyte of interest. For example, a biological affinity ligand can be bound to the fibers via a streptavidin/biotin binding system, an antibody/hapten system, a chelation system following amination of the fiber, and the like.

In one particular embodiment, the disclosed devices and methods can be utilized to separate polypeptides from each other and/or from other compounds found in a test sample, for instance compounds found in buffer solutions such as salts, other organics, urea, and detergents. The invention is not limited to this particular embodiment, however, and other SPE protocols can also be carried out with the disclosed devices including, for instance, isolation and/or concentration of analyte species such as metal ions as may be found in nuclear waste media as well as extraction of pollutants from water samples.

Following adsorption of the target analyte to the fibers, the analyte can be recovered from the solution via elution with any suitable, compatible solution to which the analyte has a higher affinity as compared to the fiber surface. Isolation and concentration of the analyte can greatly improve sensitivity of detection of the analyte, for instance via mass spectrometry methods including electrospray ionization (ESI-MS) methods and matrix-assisted laser desorption-ionization (MALDI) methods.

The disclosed invention can be further understood with reference to the following Examples.

Example 1

Capillary-channeled propylene fibers having nominal diameters of approximately 50 μm and 8 branched capillaries running along their length were examined for protein separations. The capillary-channeled fibers were obtained from Eastman Chemical, Kingsport, Tenn. from a bobbin of fibers measuring more than 1000 meters in length.

Bundles of approximately 1200 fibers were loaded co-linearly into 4.6 mm i.d., 306 mm long stainless steel tubing (available from Valco Instruments, Houston, Tex.). Bundles were passed through the column such that the general alignment of the fibers within the column was longitudinally parallel such that broadening due to eddy diffusion, i.e., tortuous paths, was expected to be minimal.

The fiber lengths were trimmed to be flush with the tubing ends, and the column ends were sealed with 0.75 mm thick, 6.35 mm diameter frits including 10 μm pores and completed with column end fittings (available from Valco Instruments). Each fiber column had a packing mass of about 1.7 grams. Column porosity determinations for the polypropylene fiber columns yielded values of approximately 0.66. The columns were flushed repeatedly with organic solvent (methanol and acetonitrile) and distilled water.

The chromatographic system consisted of a Waters (Milford Mass.) Model 600S HPLC pump with a 6 port Rheodyne injection valve (Rohnert Park, Calif.) fitted with a 10 μL injection loop. The prepared columns were mounted in place of conventional columns in the system. A Waters 2487 dual wavelength absorbance detector was employed at 216 nm, and the separations were performed at a solvent flow rate of 1.5 mL/min.

HPLC-grade water (Fisher Scientific, Pittsburgh, Pa.) was used for the preparation of the protein solutions. Each protein stock solution was prepared as a 1 ppm solution using 5:95 (ACN-water) containing 0.1% TFA. The four proteins and the TFA used in the mobile phase were purchased from Sigma Aldrich (Milwaukee, Wis.). Particular proteins were superoxidase (SOD) from bovine erythrocytes (EC No. 232-943-0), myoglobin from horse skeleton muscle (EC No. 309-705-0), hemocyanin from human, and hemoglobin from horseshoe crab. The mobile phase was prepared from HPLC-grade ACN, water, and 2-propanol. The protein test solutions were stored at 6° C.

The protein test mixture was prepared by mixing 2 mL of each protein stock solution in a 20 mL vial. The column was rinsed with mobile phase 95:5 water and (1:1) propanol-acetonitrile for 10 minutes before each injection. The separation was achieved using a gradient elution of 95:5 to 35:65 water containing 0.1% TFA (v/v)-propanol/ACN (1:1) (containing 0.085% TFA) over 70 minutes at 1.5 mL/min.

Figure 8:
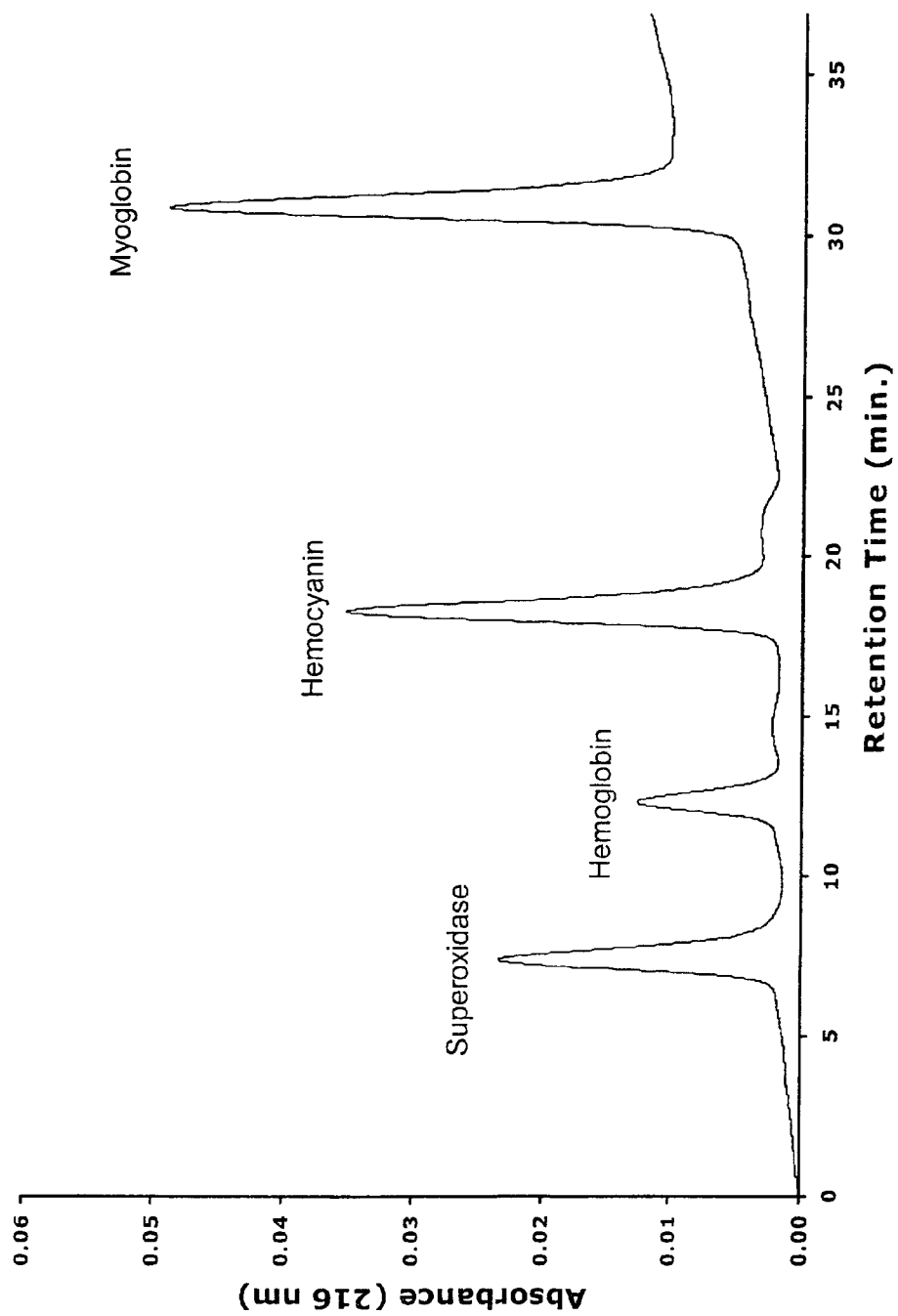
FIG. 8 illustrates the separation of a mixture of proteins utilizing a separation column comprising capillary-channeled polymer fibers as described herein.

The gradient elution chromatogram of the mixture is shown in FIG. 8. Table 1, below, summarizes the basic characteristics for the separation. As seen in the Figure, each of the peaks is very well resolved and quite symmetric in profile and the elution order does not correspond to the analyte molecular weights (31.2, 60, 75, and 17 kDa, respectively).

TABLE 1

| Protein | Retention Time | Retention Factor | Selectivity Factor | Peak half-width | Resolution | Asymmetry | PC |
|---|---|---|---|---|---|---|---|
| SOD | 7.5 | 2.3 | — | 0.95 | — | 1.4 | 4.6 |
| Hemoglobin | 12.4 | 4.4 | 1.9 | 0.86 | 1.4 | 1.09 | 8.5 |
| Hemocyanin | 18.3 | 6.9 | 1.6 | 0.85 | 1.6 | 1.08 | 13 |
| Myoglobin | 31 | 12.5 | 1.8 | 0.99 | 2.9 | 1.05 | 18 |

Example 2

Reagents used included lysozyme from chicken egg white, myoglobin from equine skeletal muscle, sodium chloride (NaCl), sodium phosphate dibasic ($Na_2HPO_4$), potassium phosphate monobasic ($KH_2PO_4$), Sigma 7-9® (tris base), and Trizma® hydrochloride (tris acid) obtained from Sigma-Aldrich (Milwaukee, Wis.). Potassium chloride (KCl) and formic acid were obtained from Fisher Chemicals (Pittsburgh, Pa.). ACS grade acetonitrile (ACN) was obtained from Mallinckrodt Baker Inc. (Phillipsburg, N.J.) and used as an organic mobile phase. Nanopure Diamond® water (18.2 MΩ/cm) from Barnstead/Thermolyne Water Wystem (Dubuque, Iowa) was used in solution preparation for buffers and proteins and aqueous mobile phases.

Extraction conduits were assembled according to a procedure as illustrated in FIG. 3. In particular, the fibers were pulled through a 0.8 mm i.d. fluorinated ethylene polypropylene (FEP) tubing (available from Cole Parmer, Vernon Hills, Ill.). A fiber loop corresponding to a total of 658, 55 μm diameter polypropylene fibers was pulled collinearly through a length of the FEP tubing about 300 mm in length. This number of fibers represents an interstitial fraction within the conduit of approximately 0.6. Compression fittings were placed on the tubing ends, the assembly placed on a high performance liquid chromatography (HPLC) system (Shimadzu LC-10AT, Tokyo, Japan) and the fibers washed alternating with acetonitrile and water (twice) for a period of 30 minutes at a flow rate of 1 milliliter per minute (mL/min).

Segments of the fiber-packed tubing were cut using a surgical grade scalpel. The FEP tubing was stretched slightly past the fiber ends to create about 6 mm of space between the fiber ends and the end of the tubing to accommodate the micropipette tip. The open end of the tube was slipped over the tip of 1 milliliter micropipette tips (Redi-Tip™, Fisher Scientific, Pittsburgh, Pa.) and was simply held in place by the compression of the tubing around the micropipette tip. The opposite end of the tubing was then cut so that 1 centimeter of fiber packed tubing was attached to the micropipette tip. Each micropipette tip was equilibrated by passing 200 microliters (μl) of 100% water through the assembly prior to use.

A 0.04 mg/mL lysozyme solution was made in a phosphate-buffered saline (PBS) matrix consisting of 140 mM NaCl, 10 mM $Na_2HPO_4$, 1.8 mM $KH_2PO_4$ and 2.7 mM KCl pH 7.3. A 50 μl aliquot of this solution was aspirated onto the 1 cm extraction conduit by drawing up the volume and pushing the volume off five times total.

The same loading procedure was also performed for myoglobin at 0.04 mg/mL in 100 mM Tris(tris(hydroxymethyl) aminoethane) buffer containing 0.0084 M Tris acid and 0.0015 M Tris base, pH 7.5.

Protein-loaded extraction conduits attached to micropipette tips were washed with a single 100 μL volume of Nanopure water to remove the ionic (salt) species. The proteins (lysozyme and myoglobin) were eluted by running a single 100 μL aliquot of 100% ACN through each extraction conduit and collecting the eluent in a centrifuge tube. The eluent was diluted to 200 μL with Nanopure® water and conditioned with formic acid for a final concentration 0.1% formic acid prior to ESI-MS analysis.

A Waters (Milford, Mass.) quadrupole-time of flight (Q-ToF micro) mass spectrometer with an ESI source was used for the protein determinations. The protein-containing solutions were injected directly to the ESI source through a Waters (Milford, Mass.) capillary liquid chromatograph (Cap LC). The flow rate was set at 2 μL/min. The ion source potential was set at 3000 volts in the positive ion mode, with the quadrupole mass filter scanned from 500 to 2500 m/z in 2 seconds. Methanol was injected between runs to prevent carryover from previous runs. The ESI mass spectra for the proteins in the original buffer media and post-extraction were compared on both a qualitative and quantitative basis. Equal amounts of the proteins were injected throughout the experiment to ensure a non-biased comparison of spectral quality, signal to noise ratios, etc.

The practical metrics in assessing the ability of the disclosed method for purifying protein solutions include the production of well-distinguished multiply-charge ion species, with high intensities and the ability to deconvolute those spectra to yield high fidelity molecular ions/weights. Shown in FIGS. 9 and 10 are the ESI mass spectra that were obtained from the lysozyme in the initial PBS matrix and that from the protein eluted from the fiber-filled tubing attached to the micropipette tip. The mass spectrum of the protein in the buffer solution (FIG. 9A) shows effectively a continuum of signals across the mass range, with only two discernable peaks that can be attributed to ionized protein. On the other hand, the mass spectrum of the protein post-extraction (FIG. 10A) is composed solely of protein related species across this mass range. This illustrates the fact that the buffer salts compete for ionization and removing salts enhances the population of protonated lysozyme molecules. In fact, the integrated total ion chromatograms for the two solutions are virtually identical. As a further point of comparison, the signal-to-noise ratios of the signature lysozyme ions at m/z=1590 Da are about 2.5 for the buffer solution and about 125 for the extracted protein.

Having acquired the raw ESI spectra of the protein solutions, the molecular weight of the protein was deconvoluted using the Waters® Micromass® MaxENT™ 1 algorithim. The resultant molecular ion spectra are presented in FIGS. 9B and 10B, respectively. In the case of the buffer solution, a large number of possible molecular ions are identified, including one near the presumed molecular weight. As can be seen with reference to FIG. 9B, however, the actual assignment of this peak as a unique value is not valid. The spectral purity of the extracted protein yields an unambiguous molecular ion spectrum (FIG. 10B), with the identified molecular weight being identical to that of the neat protein in acidified ACN and only 35 ppm different from the manufacturer's certificate.

Tris(tris(hydroxymethyl)aminoethane) is commonly used as a buffer to stabilize proteins in solution. Different from the case of the PBS matrix, tris is an organic buffer that has some modest amount of alkyl character that may have an affinity for a polypropylene fiber surface. In addition, the hydroxide moiety might also have some propensity for hydrogen bonding with the stationary phase. The mass spectra presented in FIGS. 11 and 12 are derived for myoglobin (equine skeletal muscle) at a concentration of 0.04 mg/ml in 100 mM tris buffer (FIG. 11) and that for the myoglobin following solid phase extraction on the capillary-channeled fiber phase (FIG. 12A). The most remarkable feature of the mass spectrum of the protein in the buffer-matrix (FIG. 11) is the presence of multiple cluster peaks that display a mass unit difference of 157 between the major peaks; equal to the monoisotipic mass of tris-acid ($C_4H_{11}NO_3HCl$). This clearly demonstrates that tris-buffer ionizes readily and forms clusters in the ESI process. Buffer ionization occurs, in fact, to the exclusion of protein ionization as none of the peaks present in the fiber-extracted protein spectrum (FIG. 12A) are present in the spectrum of the buffer-containing solution. In this situation, deconvolution produces no meaningful protein information (FIG. 12B). In the case of the fiber-extracted solution, the MaxENT™ 1 algorithim reveals that using the molecular weight spectrum shown in FIG. 12B, computing a molecular weight for this myoglobin specimen to be 16,951 Da. As in the case of the lysozyme extraction, the molecular weight computed here is identical to that of the myoglobin obtained for a neat, acidified ACN solution.

While a preferred embodiment of the invention has been described using specific terms, such description is for illustrative purposes only, and it is to be understood that changes and variations may be made without departing from the spirit or scope of the following claims.

What is claimed is:

1. A solid phase extraction process for a test sample comprising one or more members of an analyte class, comprising:
    contacting a plurality of polymeric fibers with the test sample, each polymeric fiber being configured with a plurality of co-linear capillaries along the entire length of the surface of the fiber, the polymeric fibers being held in a region of a micropipette tip defining a wall, the micropipette tip being free of any containment barrier or wall projections for holding the polymeric fibers in place, the polymeric fibers being nominally aligned with one another and being maintained within the micropipette tip by packing of the fibers against one another and the wall, the fibers being packed tightly enough so as to ensure they will be securely maintained in the micropipette tip during the solid phase extraction process, the one or more members of the analyte class being adsorbed onto the surfaces of the polymeric fibers; and
    eluting the one or more members of the analyte class off of the polymeric fibers so as to concentrate the one or more members of the analyte class.

2. The solid phase extraction process of claim 1, wherein the test sample is less than about 10 milliliters in volume.

3. The solid phase extraction process of claim 1, wherein the analyte class is polypeptides.

4. The solid phase extraction process of claim 3, wherein the test sample is a buffer solution.

5. The solid phase extraction process of claim 1, wherein the surface of each polymeric fiber is functionalized and the one or more members of the analyte class exhibit an increased affinity for the fiber due to the functionalization.

6. The solid phase extraction process of claim 1, wherein the plurality of polymeric fibers are disposed along the axial length of the micropipette tip.

7. The solid phase extraction process of claim 1, wherein the micropipette tip is removably attachable to a fluid flow device.

8. The solid phase extraction process of claim 7, wherein the fluid flow device is an aspirator, a pump or an electro-osmosis device.

9. The solid phase extraction process of claim 1, wherein the test sample contacts the surface of the fibers via capillary action of the test sample through the capillaries of the fibers.

10. The solid phase extraction process of claim 1, wherein the test sample is at a location that is remote to a laboratory testing facility and the solid phase extraction is carried out at the remote location.

11. The solid phase extraction process of claim 1, wherein the fibers comprise a polyolefin, a polyamide, a polyester, or a combination of at least two of the foregoing.

12. The solid phase extraction process of claim 1, wherein the one or more members of the analyte class is adsorbed onto the surface of a fiber via an ionic affinity between the one or more members of the analyte class and the surface of the fiber.

13. The solid phase extraction process of claim 1, wherein the one or more members of the analyte class is adsorbed onto the surface of a fiber via a hydrophobic or a hydrophilic affinity between the one or more members of the analyte class and the surface of the fiber.

14. The solid phase extraction process of claim 1, the plurality of polymeric fibers further comprising a ligand for the analyte, wherein the one or more members of the analyte class is adsorbed onto the surface of a fiber via affinity between the analyte and the ligand.

15. The solid phase extraction process of claim 1, wherein the interstitial fraction within the region of the micropipette tip holding the polymeric fibers is between about 0.15 and about 0.7.

16. The solid phase extraction process of claim 1, wherein the test sample comprises multiple members of an analyte class, the multiple members of the analyte class being eluted together off of the polymeric fibers.

17. The solid phase extraction process of claim 16, wherein the multiple members of the analyte class are eluted by use of acetonitrile.

* * * * *